US012594044B2

(12) United States Patent
König et al.

(10) Patent No.: US 12,594,044 B2
(45) Date of Patent: Apr. 7, 2026

(54) METHOD FOR RECORDING A LARGE-AREA X-RAY IMAGE

(71) Applicant: Ziehm Imaging GmbH, Nuremberg (DE)

(72) Inventors: Thomas König, Nuremberg (DE); Johannes Wagner, Stegaurach (DE)

(73) Assignee: Ziehm Imaging GmbH, Nuremberg (DE)

( * ) Notice: Subject to any disclaimer, the term of this patent is extended or adjusted under 35 U.S.C. 154(b) by 121 days.

(21) Appl. No.: 18/458,046

(22) Filed: Aug. 29, 2023

(65) Prior Publication Data

US 2024/0065648 A1 Feb. 29, 2024

(30) Foreign Application Priority Data

Aug. 30, 2022 (DE) ..................... 10 2022 003 163.9

(51) Int. Cl.
A61B 6/46 (2024.01)
A61B 6/00 (2006.01)
(Continued)

(52) U.S. Cl.
CPC ............ A61B 6/4441 (2013.01); A61B 6/025 (2013.01); A61B 6/027 (2013.01); A61B 6/469 (2013.01);
(Continued)

(58) Field of Classification Search
CPC ....... A61B 6/035; A61B 6/4441; A61B 6/481; A61B 6/025; A61B 6/027; A61B 6/465;
(Continued)

(56) References Cited

U.S. PATENT DOCUMENTS

2012/0257714 A1 10/2012 Graumann et al.
2016/0048983 A1* 2/2016 Zamyatin .............. G06T 11/006
382/130
(Continued)

FOREIGN PATENT DOCUMENTS

WO WO-2008078259 A2 * 7/2008 ............. A61B 5/417

*Primary Examiner* — Uzma Alam
*Assistant Examiner* — Mamadou Faye
(74) *Attorney, Agent, or Firm* — Knobbe, Martens, Olson & Bear LLP

(57) ABSTRACT

Method for providing a large-area x-ray image of an object mounted by means of an object platform and providing additional synthetic x-ray projections, comprising Recording of a plurality of x-ray projections by means of an x-ray device, wherein the plurality of x-ray projections are recorded during a linear movement of the object platform and/or the x-ray device; preparation of at least one tomographic volume from the plurality of x-ray projections; preparation of at least one first synthetic forward projection from the at least one tomographic volume, wherein the at least one synthetic forward projection yields a large-area x-ray image; representation of the large-area x-ray image on a suitable display device; selection and/or marking of an area of interest within the large-area x-ray image; preparation of at least one second synthetic forward projection comprising the area of interest; representation of the at least one second synthetic forward projection on a suitable display device; characterised in that the at least one second synthetic forward projection is prepared in a projection geometry that corresponds to the current orientation of the x-ray device in space.

20 Claims, 5 Drawing Sheets

(51) Int. Cl.
   *A61B 6/02*          (2006.01)
   *G06T 11/00*        (2006.01)

(52) U.S. Cl.
   CPC ............ *A61B 6/481* (2013.01); *A61B 6/5205*
         (2013.01); *A61B 6/5223* (2013.01); *G06T*
                                  *11/005* (2013.01)

(58) Field of Classification Search
   CPC ... A61B 6/5205; A61B 6/5223; A61B 6/5235;
            A61B 6/505; G06T 11/005; G06T 11/006
   See application file for complete search history.

(56)                    References Cited

U.S. PATENT DOCUMENTS

| | | |
|---|---|---|
| 2019/0117180 A1 | 4/2019 | Gemmel et al. |
| 2019/0175131 A1 | 6/2019 | Duewer |
| 2021/0093271 A1 | 4/2021 | Ritschl |
| 2021/0270755 A1* | 9/2021 | De Beenhouwer .... G06N 20/00 |
| 2021/0304402 A1* | 9/2021 | Morgas ................. G06N 20/00 |
| 2023/0169753 A1* | 6/2023 | Helm ..................... G06V 10/40 |
| | | 382/103 |
| 2023/0274473 A1* | 8/2023 | Hua .......................... G06T 5/70 |
| | | 382/131 |

* cited by examiner

METHOD FOR RECORDING A LARGE-AREA X-RAY IMAGE

BACKGROUND

Field

The invention concerns a method for recording a large-area x-ray image.

Description of the Related Art

X-ray devices, for example mobile or stationary C-arms, can only image a limited area of a patient on a 2D X-ray image. This area is mainly determined by the size of the x-ray detector, for example a flat panel detector or an image intensifier, for example 20×20 cm² or 30×30 cm². In most cases a simple x-ray image record is sufficient. However, there are also cases that profit from images that go beyond the size of the detector. These include, for example, the representation of spinal columns and abnormal changes of them, such as scoliosis (curvatures along the long axis) and, for example, tracking contrast agent injections, for example along an entire leg, or in aortal interventions, which below are called bolus chase or bolus.

The cases noted above are interventional applications, in which a comparison before, during, and after an operative intervention is particularly of interest. In the case of orthopaedic applications one can in general start from a static view, so that by changing the image section, in particular by shifting the patient position, for example by moving an x-ray platform, x-ray images of different areas of the patient can be recorded.

Regardless of how the changing of the image section is implemented, it initially involves a single x-ray image or isolated x-ray images, which exist without reference to one another and can be interpreted only individually or as a sequence. It would be advantageous, in particular when the position of the patient platform is changed, to combine the individual x-ray images continuously into a large overall image.

An obvious possibility for generating a large-area x-ray image is known from DE 102019001988. In this case the individual images are simply joined together, for example, assembled by an algorithm for image registration, especially so-called "stitching" processes. However, if at least two x-ray images are simply combined, artifacts can arise in the overall image that is to be read. The sources of this may be the unavoidable cone beam geometry of the x-ray device, as well as the use of planar (flat) detectors in this geometry. When using an x-ray point source, as in traditional x-ray tubes, the corresponding areas in the images (e.g. two) to be combined are recorded from two different view angles and thus different representations of the same objects result. It turns out from the different representations of the same objects that the x-ray images cannot be brought sufficiently or consistently into congruency by means of a simple image registration process.

Furthermore, the use of planar detectors in combination with an x-ray point source, which generates divergent x-ray beams, causes objects or patient areas to become the more distorted the further they are from the central point of the detector. This likewise produces a situation where a region that, for example, lies at the edge of the detector in one image and at its middle in another image cannot be consistently represented in an overall image.

Furthermore, when there are scene changes in the recording, for example due to injection of contrast agents, image registration can no longer be successfully carried out, since due to the change of scenes, for example due to spreading of the contrast agent, sufficiently corresponding image areas can no longer be produced in the image sequence.

DE10 2015 204 957 discloses a tomosynthesis system that indicates depth information in color coded form.

DE 10 2018 212 389 discloses a tomosynthesis system that moves along the patient, wherein a colimator changes the cone beam angle in dependence on the position of the system.

The selection of an area of interest on a touch display or GUI and the ensuing method of object positioning and the x-ray source at exactly this position are known from DE102020209714. In contrast to the present invention, object platform and x-ray source are moved at the same time and in different directions.

Likewise, selection of an area of interest on a touch display or GUI and the ensuing method of object positioning and/or the x-ray source at exactly this position are known from EP3669942. However, in this case plural regions are selected and marked with an adjustable marker.

SUMMARY

To solve the problem, a method having the following steps is used for recording a large-area x-ray image, in particular of a patient, on an object platform by means of an x-ray device that generates x-rays in a fan beam geometry:

a. recording a first x-ray image using a first recording geometry;

b. recording at least one second x-ray geometry [sic; image] using a second x-ray geometry, wherein the first x-ray image partially overlaps the second x-ray image;

c. reconstruction of a tomosynthetic volume from the recordings of the at least two x-ray images;

d. preparation of synthetic forward projections from the tomosynthetic volume, wherein the totality of the synthetic forward projections yields a large-area x-ray image;

e. representation of the large-area x-ray image on a display device;

f. marking of an area of interest on a suitable display device, g. preparation of a synthetic forward projection of the area of interest as a preview image, based on an evaluation of the relative position of the x-ray device and the object platform, so that the preview image is prepared in a recording geometry that corresponds to the current orientation of the x-ray device in space.

DETAILED DESCRIPTION

Figure 1:
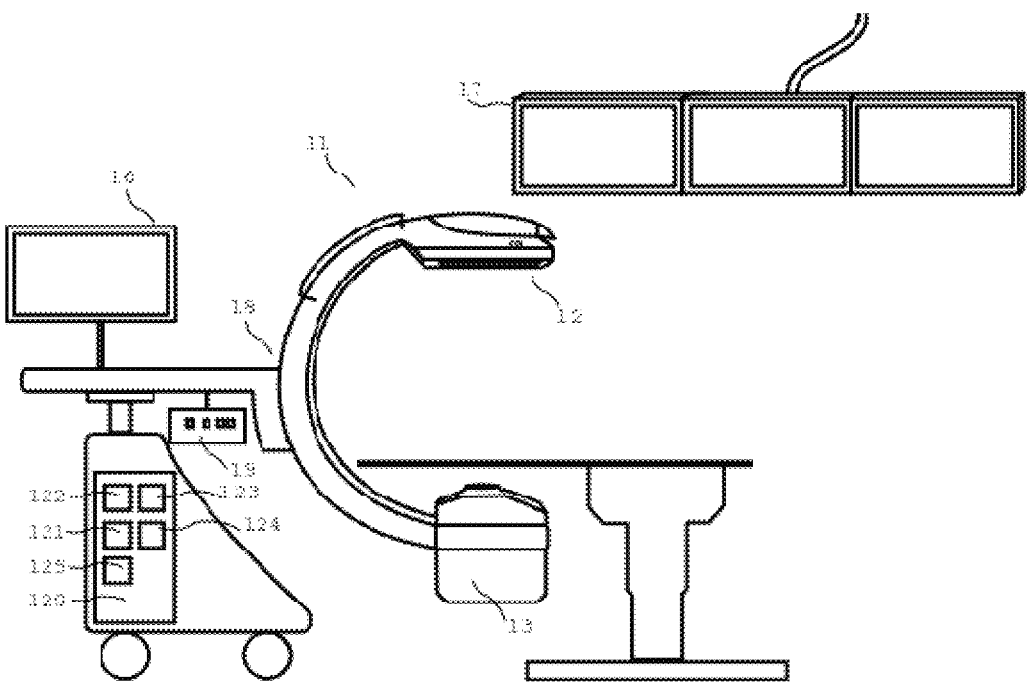
FIG. 1 shows a device according to the invention in the embodiment of a mobile C-arm.

The aim of the invention is thus to make available a method that provides, from at least two x-ray images, an artifact- and distortion-free large-area x-ray image which can be displayed on suitable display devices such as screens, displays, and/or computers. Preferably, said display devices have a touch, front-end, or GUI function. The object platform indicated below can correspond to a patient platform or any other suitable positioning device for patients and/or objects.

The aim of the invention is achieved according to the invention by the features of the independent claims. Advantageous embodiments are specified in the dependent claims.

Preferably, the invention is implemented using software with the purpose of providing a large-area x-ray image. The largely software controlled implementation of the method has the advantage that methods for image recording systems already being used for this purpose can be upgraded simply by a software update in order to operate in the manner according to the invention. In this respect the aim is also achieved by a corresponding computer program product with a computer program which can be stored directly in a memory device of an x-ray device, for example a C-arm x-ray device, with program sections to execute all steps of the method according to the invention when the computer program is executed in the control device. In addition to the computer program, such a computer program product may optionally comprise additional components such as documentation and/or additional components, including hardware components for using the software.

A computer readable medium, for example a memory stick, a hard disk, or an otherwise transportable or integrated data carrier, on which program sections of the computer program which can be read and executed by a computer unit of the control device are stored, can serve for transport to the control device and/or to the memory on or in the control device. A connection to a hospital information system connected to a network, to a radiology information system or to a global network, in which systems are stored the program sections of the computer program which can be read in and executed by a computer unit of the control device, can also be used for the transport. The computer unit can have, for example, one or more cooperating microprocessors or the like for this purpose.

The method according to the invention is based on a first record of an x-ray image, which was made using a first recording geometry. The recording geometry concerns in particular the position (location) of the x-ray device with respect to the object platform, wherein the recording geometry is to be changed by a rotation or by a linear shift of the position of the x-ray device with respect to the object position, for example by a raising or lowering of the x-ray generator and/or the x-ray detector, and, for example, by a linear shift of the x-ray generator parallel and/or perpendicular to a plane. The method according to the invention is based on the recording of a second x-ray image, wherein the recording geometry of the first x-ray image and the recording geometry of the second x-ray image are different from each other. Preferably, the recording geometry of the second x-ray image differs from the recording geometry of the first x-ray image by a linear displacement along the direction of the object platform. According to the method according to the invention it is irrelevant whether the change of the recording geometry results from a change of position of the x-ray device or from a change of position of the object platform (relative change of position).

Then, a tomosynthetic 3D volume is reconstructed from the first and the second x-ray images, wherein the tomosynthetic 3D volume, in contrast to 3D computer tomography, has an incomplete angular coverage and thus limited depth resolution. The tomosynthetic volume in this case can be generated by known methods, in particular with the aid of a filtered or unfiltered back projection, an iterative or algebraic reconstruction process, or even by using a machine learning process trained for this purpose. Optionally, a calibration of the C-arm, the object platform, and/or in particular the relative positioning or alignment of the two to each other, is envisioned. Alternatively, a reconstruction can be carried out even without such a calibration.

After the reconstruction of a tomosynthetic 3D volume, synthetic forward projections are prepared from the tomosynthetic volume, preferably in parallel or fan beam geometry, wherein the totality of all synthetic forward projections combined yields a large-area x-ray image. The resulting large-area x-ray image is then displayed on a display device. Furthermore, alternatively executing the forward projections as cone beam geometry is envisioned.

In alternative embodiments the method according to the invention comprises a zoom functionality, in particular for the x-ray image, for example for a magnification or reduction of areas of the large-area x-ray image, wherein an image need not necessarily correspond to a recording, but rather an area can consist of several x-ray recordings.

Then, the method according to the invention calls for a synthetic forward projection to be displayed on a display device as a preview or preview image on the basis of an evaluation of the relative position of the x-ray device and the object platform. In the computation of the preview image the position of the x-ray device relative to the object platform is evaluated so that the preview image corresponds to an x-ray image recorded in this position, in particular the recording geometry existing at that point. Therefore, according to the invention it is provided that this synthetic forward projection is preferably prepared in a cone beam geometry which takes into account the spacing of the x-ray focus and x-ray detector. This is advantageous in order to generate a preview image that is as close as possible to an actually acquired x-ray image. A preferred embodiment of the method according to the invention calls for the preview image to be updated automatically in the adjustment of the orientation of the x-ray device in space by the user, so that the preview image further reflects the current orientation of the x-ray device.

To reduce the radiation dose for patients a preferred embedment of the method according to the invention further calls for generation of a preview image, which does not correspond to the current relative position of the x-ray device and the object platform, but rather corresponds to one that is especially advantageous for the selected medical procedure. Here it is envisioned that users will select a region of interest corresponding to the requirements and based on the large-area x-ray image, and then an automatic, preferably motorized, adjustment of the object platform and/or the x-ray device will take place so that the desired recording geometry will result from the adjustment.

Another preferred embodiment calls for the computation of a movement of the x-ray device and/or the object platform from the receiving area of interest to take place under the stipulation that after completing the movement a projection geometry relative to the object exists, which then enables the preparation of an x-ray projection, which at least approximately corresponds to the second synthetic forward projection. Then the computed movement is evaluated to see if it can be implemented by the kinematic boundary conditions of the x-ray device and/or the object platform. Finally the movement will be carried out only if it can be carried out.

Otherwise, an indication is output in visual and/or acoustic form if the movement cannot be carried out.

In alternative embodiments the above steps, however, can only be carried out if a security criterion has been satisfied, in particular when, on the basis of the determined relative position, it is assured at least approximately that all frequencies required for said forward projection are present in the Fourier representation of the tomosynthetic volume and thus the forward projection can be prepared largely free of artifacts. If this is not the case, a report can be output on the display device indicating that a selected recording geometry is not suitable for preparation of a preview image.

In alternative embodiments the method according to the invention comprises functions for measurement of lengths and/or angles on the synthetically generated forward projections, in particular on the large-area x-ray image.

In alternative embodiments the method according to the invention can display a sequence of the recorded x-ray images on a display device, for example in the form of a film sequence, preferably combined with highlighting, in particular highlighting of a portion of the sequence that corresponds to the current position of the x-ray device with respect to the object platform.

In alternative embodiments of the method according to the invention it is provided that, based on the current velocity of position change, for example of the movement of the patient platform or the movement of the x-ray device or the relative movement between x-ray device and patient platform, adjustment of the timewise pulse rate and pulse length of the x-ray device can take place, preferably in order to determine a sampling rate suitable for the tomosynthesis and to prevent or diminish motion blurring in the recorded x-ray images.

The method according to the invention can also be used in the case of a change of scene (scene change) during the recording of the C-arm images for the large-area x-ray image. In particular, said scene changes can result from the injection of contrast agent or agents. In this case visible artifacts may arise in the recorded x-ray images, since inconsistencies result between the individual x-ray images because of timewise changes, in particular a contrast agent dynamic changing over time. This results because the scene changes are reproduced at different time points in the x-ray images, for example because of the inflow and outflow contrast agent. Before preparing the large-area x-ray image the relevant scene changes are identified on the recorded x-ray images, thus those that have a dynamic development, for example in the case of injected contrast agents the blood vessels, wherein the blood vessels are at least partially filled with contrast agent. According to the invention, the relative movement of x-ray device and object platform here is not considered a scene change, since it is appropriately handled within the scope of the tomosynthesis. Relevant scene changes can be advantageously identified here by means of image processing methods. Classic methods as well as a priori trained machine learning methods that in each case are matched to the usage case, for example to the flow of a contrast agent, can be used for this. Preferably, in each case a set containing at least one derived projection, but preferably a plurality of such projections, is prepared from a starting x-ray projection. The derived projections in this case correspond to specific classes of image contents, in particular the image contents without scene changes and one or more classes of scene changes, for example blood vessels filled with contrast agent. In these alternative embodiments of the method according to the invention the identified scene changes are then considered as follows:

Based on the prepared sets, at least one tomosynthetic reconstruction is prepared from the at least one derived projection, namely based on the derived projections belonging to a specific class. In one possible embodiment of the method according to the invention a tomosynthetic reconstruction is prepared solely taking into account the class that corresponds to those image areas that do not have any scene change, for example, the surrounding anatomy of a blood vessel, in particular bone and/or soft tissue. This tomosynthetic reconstruction is the basis for preparation of a large-area x-ray image by means of forward projection, which can be interpreted as background.

In alternative embodiments of the method according to the invention other derived projections can be the basis for preparation of a tomosynthetic reconstruction, which contains only one specific class of scene changes, for example blood vessels containing contrast agent. It is advantageous for the steps of the method described above to have prior knowledge of whether scene changes may be present and to evaluate them by computer. This can take place, for example, through the selected organ program, so that only in the appropriate case will the method according to the invention look for scene changes. For example, scene changes would not be looked for in the preparation of spinal column recordings, while one would look for a scene change in the recording of a bolus, for example, in the case of injected contrast agent in the vessels of a patient.

The derived projections can be calculated by various methods, in particular by means of image processing technical methods. In the case of regions containing contrast agents these can be detected, for example, through a change of brightness. Alternatively, dark image regions that have sharp boundaries and are oriented in the direction of movement are identified as contrast agent-containing blood vessels, for example by means of a structure tensor. Broadly speaking, machine learning methods, for example deep learning, in particular convolutional neural networks, can be trained to identify, for example, areas with a scene change over the image sequence. A coordinate transformation between successive images can take place in this case, in particular while evaluating position, angle, and/or velocity codes, for example, to identify brightness changes.

In these embodiments the synthetic forward projection then can be generated, in particular in parallel beam or fan beam geometry for all tomosynthetic reconstructions. Once again, the large-area 2D x-ray image can thus be displayed with and without scene changes, for example blood vessels containing contrast agent. In particular it is possible to switch between the available displays, for example, to fade in and fade out the contrast agent-containing vessel tree or the patient background.

The method according to the invention is based on a first recording of an x-ray image, which was made using a first recording geometry. The recording geometry concerns in particular the position (location) of the x-ray device with respect to the object platform, wherein the recording geometry is to be changed by a rotation or by a linear shift of the position of the x-ray device with respect to the object position, for example by a raising or lowering of the x-ray generator and/or the x-ray detector, and, for example, by a linear shift of the x-ray generator parallel and/or perpendicular to a plane. The method according to the invention is based on the recording of a second x-ray image, wherein the recording geometry of the first x-ray image and the recording geometry of the second x-ray image are different from each other. Preferably, the recording geometry of the second x-ray image differs from the recording geometry of the first x-ray image by a linear displacement along the direction of the object platform. According to the method according to the invention it is irrelevant whether the change of the recording geometry results from a change of position of the x-ray device or from a change of position of the object platform (relative change of position).

Then a tomosynthetic 3D volume is reconstructed from the first and the second x-ray image, wherein the tomosynthetic 3D volume has limited depth resolution due to the method or equipment. The tomosynthetic volume can in this case be generated by known methods, in particular with the help of a filtered back projection, an iterative or an algebraic reconstruction method, or even by using a machine learning method trained for this purpose. Optionally it is provided in this case to use a calibration of the C-arm, the patient platform, and in particular the relative positioning or alignment of the two to each other. Alternatively, a reconstruction can be carried out even without such a calibration.

After the reconstruction of a tomosynthetic 3D volume the synthetic forward projections are prepared from the tomosynthetic volume, preferably in parallel or fan beam geometry, wherein the totality of all synthetic forward projections combined yields a large-area x-ray image. The resulting large-area x-ray image is then displayed on a display device. Further, it is provided in alternative embodiments to conduct the forward projection alternatively in parallel, fan, or cone beam geometry.

The invention is explained in more detail by means of the following drawings.

In FIG. 1 a device according to the invention is schematically shown in the form of a mobile C arm 11, which is intended for implementation of the method according to the invention.

The C-arm 11 carries at one end an x-ray generator 13 and, at the other end and opposite from the x-ray generator 13, an x-ray image detector 12; for example this can be a flat panel detector or an x-ray intensifier. The C-arm 11 can be adjusted under the control of a motor in a plurality of axes in space, the axes having sensors for detecting the extent of the adjustment.

Further, the device comprises an x-ray processing unit 121, a memory unit 122, a control unit 123, and a network interface 124. By means of the network interface 124, data, such as image data sets and results of the method according to the invention, can be distributed or made available in a network.

The x-ray processing unit 121 comprises a control unit 122, on which the two or three dimensional image data sets used for the method according to the invention can be stored or loaded. These image data sets can either be loaded from a server or recorded by means of the C-arm 11 before or during an intervention. The memory unit further comprises instructions which are used for carrying out the method according to the invention by means of a computing unit.

Further, the device can comprise a GUI, with an image output unit (16, 17) and an input unit 19, with which appropriate settings for the image processing unit 121 can be managed in the corresponding organ programs.

Figure 2:
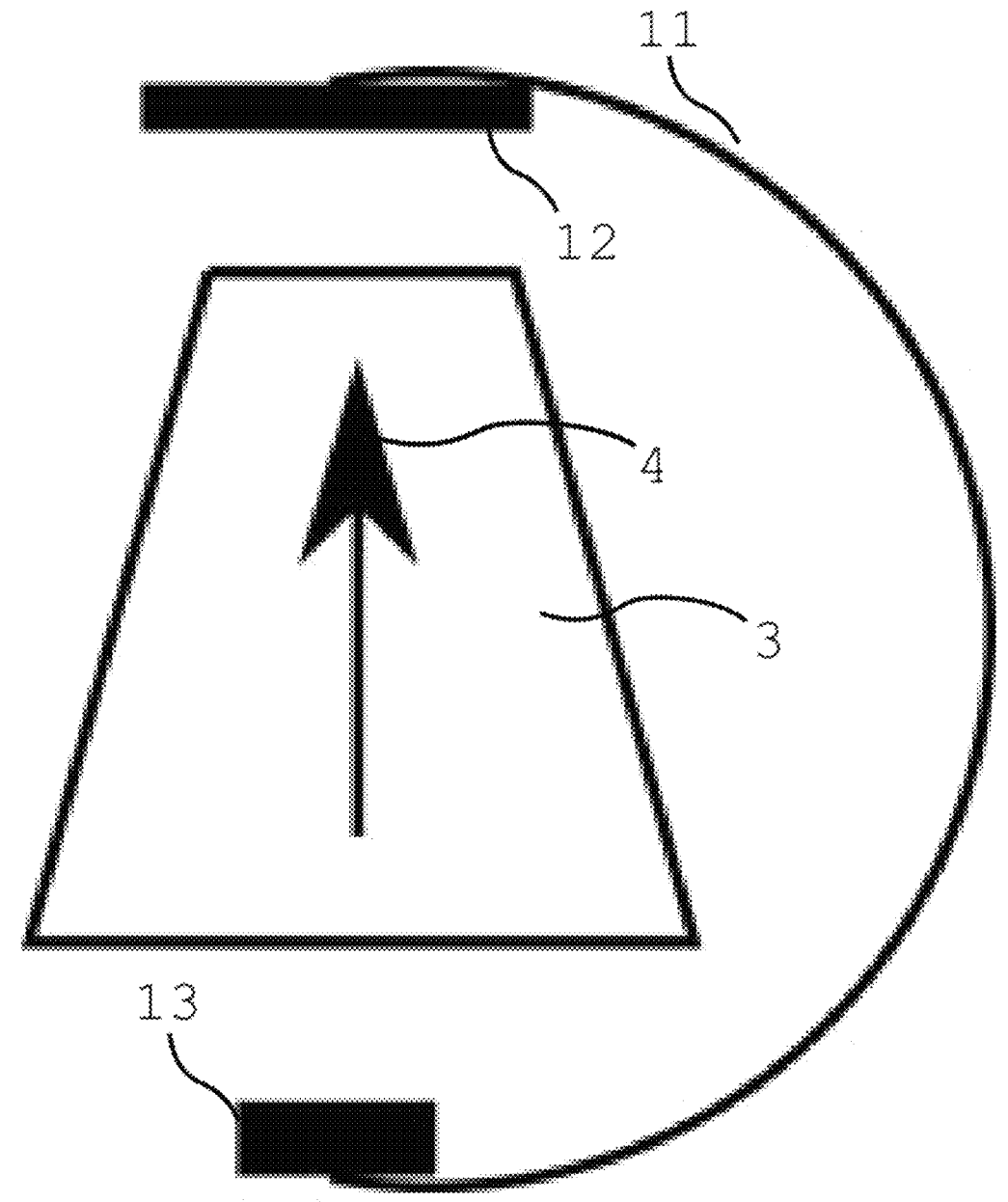
FIG. 2 schematically shows the patient platform procedure.

In FIG. 2 a device according to the invention is schematically shown in the form of a mobile C-arm 11, together with an object platform 3 that is positionable/shiftable/movable in a plurality of directions of movement 4. The object platform 3 can be moved back and forth by the C-arm 11, wherein its axes have sensors to detect the extent of the movement.

Figure 3:
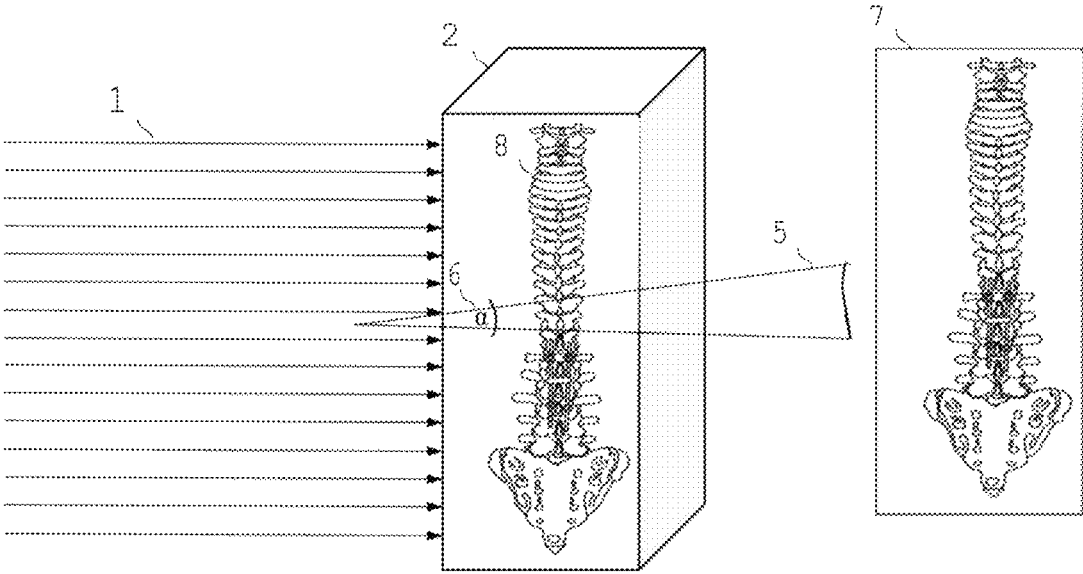
FIG. 3 discloses the synthetic forward projection in parallel and cone beam geometry.

In FIG. 3 the synthetic forward projection can be seen as a large-area x-ray image. In this case after preparing the tomosynthetic volume 2, one or more synthetic forward projections are prepared from it by sending parallel beams 1 through the tomosynthetic volume 2 via software or in a computer program in order to make available the large-area x-ray image, or panoramic image 7. Now only the area of interest 9 is selected from this panoramic image 7 shown on the image screen and the preview image 10 is computed for it, preferably in cone beam geometry, with the aperture angle of the central projection 6, which then can be represented on a suitable display device 16 and wherein the preview image 10 is prepared in projection geometry that corresponds to the current orientation of the x-ray device in space. According to the invention this display device 16 can be a touch screen or GUI-capable image screen. Now by means of an input instruction the object platform and/or the C-arm 11 can be moved directly to this area of interest 9 and at this point an actual x-ray image, which approaches the previously prepared preview image and which can be displayed according to the invention, can be prepared.

Figure 4:
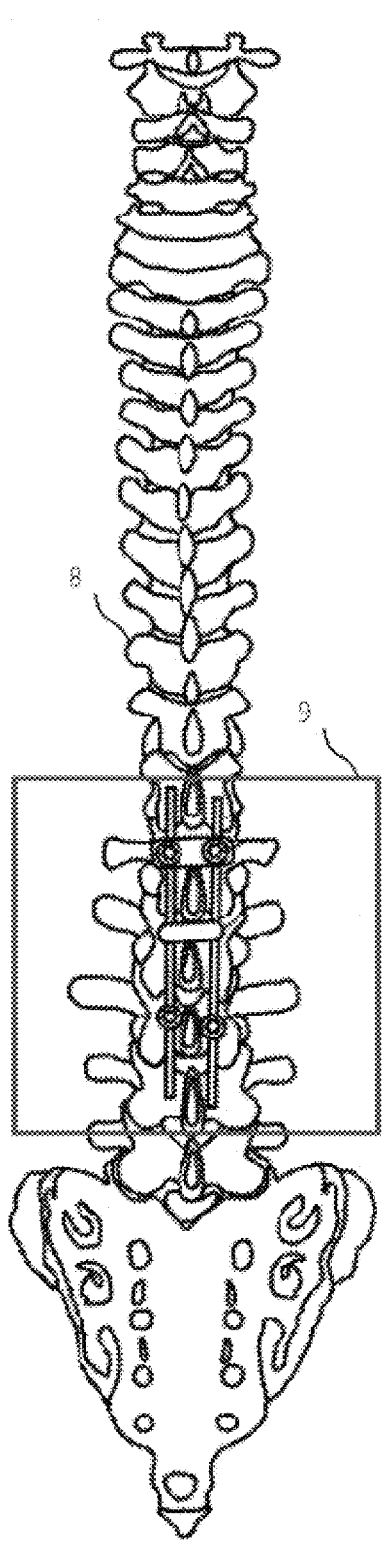
FIG. 4 schematically shows the object to be imaged, including an area of interest.

FIG. 4 shows the large-area x-ray image 7 and the selected area of interest 9.

Figure 5:
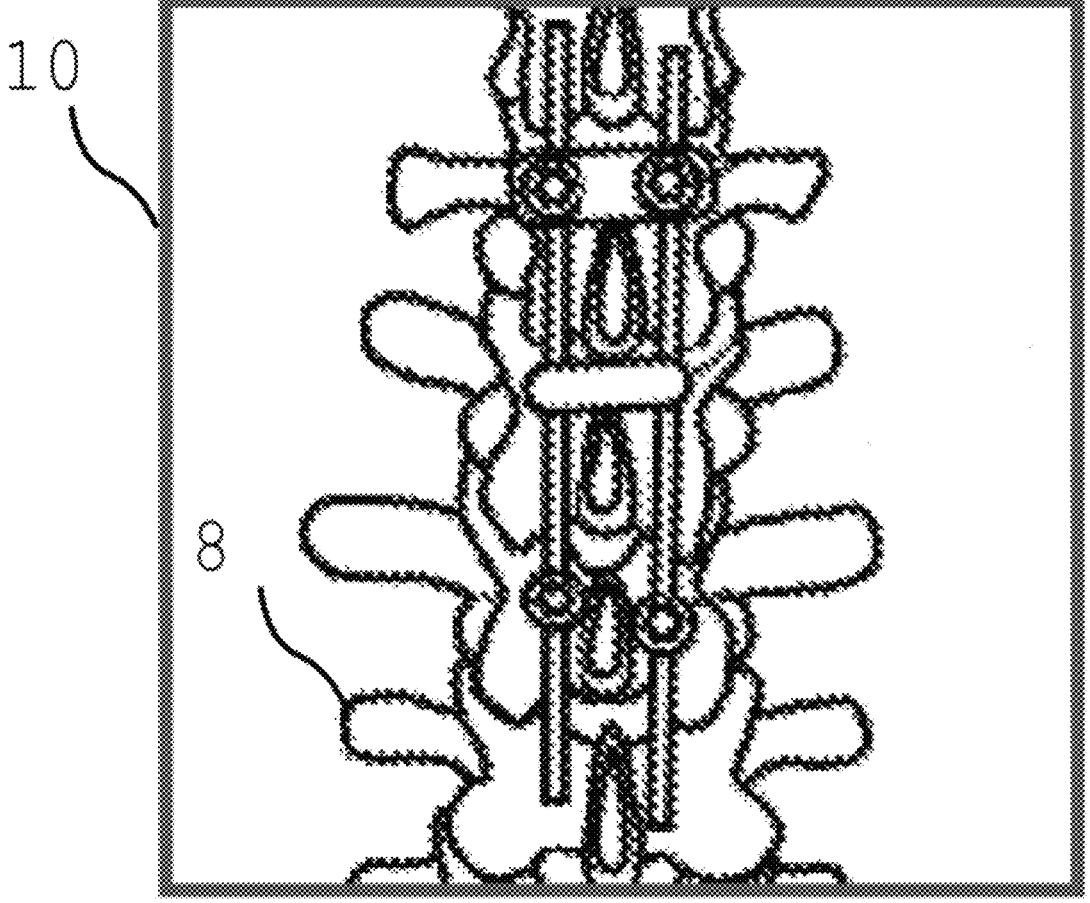
FIG. 5 shows the preview image generated to the area of interest.

FIG. 5 shows the preview image 10 of the object 8 that is to be x-rayed, which was generated according to the invention from the area of interest 9 and displayed.

LIST OF REFERENCE NUMBERS

1 Parallel projection or projection in parallel beam geometry
2 Tomosynthetic volume
3 Object platform
4 Direction of movement
11 C-arm
12 X-ray image detector
13 X-ray generator
16, 17 Image output unit
19 Input unit
121 Image processing unit
122 Memory unit
123 Computer unit
124 Network interface
5 Central projection or projection in cone beam geometry
6 Aperture angle of central projection
7 Large-area x-ray image or panoramic image
8 Object
9 Area of interest
10 Preview image

The invention claimed is:

1. A method for provision of a large-area x-ray image of an object mounted by means of an object platform and provision of additional synthetic x-ray projections, comprising:
recording a plurality of x-ray projections by an x-ray device, wherein the plurality of x-ray projections are recorded during a linear movement of the object platform and/or the x-ray device;
preparing at least one tomographic volume from the plurality of x-ray projections;
preparing at least one first synthetic forward projection from the at least one tomographic volume, wherein the at least one synthetic forward projection yields a large-area x-ray image;
representing the large-area x-ray image on a suitable display device;
receiving a selection and/or marking of an area of interest within the large-area x-ray image;
calculating a movement of the x-ray device and/or the object platform based at least in part on the received area of interest under the stipulation that after executing the movement, a projection geometry relative to the object results, which then enables the preparation of an x-ray projection that at least approximately corresponds to at least one second synthetic forward projection comprising the area of interest;

preparing at least one second synthetic forward projection comprising the area of interest; and representing the at least one second synthetic forward projection on a suitable display device;

wherein the at least one second synthetic forward projection is prepared in a projection geometry that corresponds to a current orientation of the x-ray device in space after the movement.

2. The method of claim 1, wherein the linear movement of the object platform and/or the x-ray device is overlain by an additional movement.

3. The method of claim 1, wherein the linear movement of the object platform and/or the x-ray device is detected by measurement of position and/or orientation data, and wherein the at least one tomographic volume is prepared based at least in part on the measured position and/or orientation data.

4. The method of claim 1, wherein the at least one tomographic volume is prepared based at least in part on a previously done calibration of a recording geometry.

5. The method of claim 1, wherein the at least one second synthetic forward projection is prepared in a cone beam geometry.

6. The method of claim 1, further comprising:

evaluating the calculated movement to determine if the achieved motion is feasible in accordance with one or more kinematic boundary conditions of the x-ray device and/or the object platform; and executing the calculated movement if it is determined that the calculated movement is feasible, or not executing the movement and/or outputting an indication if it is determined that the calculated movement is not feasible.

7. The method of claim 1, wherein a zoom function is made available for the large-area x-ray image and/or the second synthetic x-ray projection.

8. The method of claim 1, wherein functions for measurement of lengths and/or angles are made available on the representation of the large-area x-ray image and/or the second synthetic forward projection.

9. The method of claim 1, wherein an object area represented by the second synthetic forward projection is marked at least approximately in the representation of the large-area x-ray image.

10. The method of claim 1, wherein scene changes caused by object changes are taken into account.

11. The method of claim 10, wherein the at least one tomographic volume is prepared from derived projections, which contain at least one specific class of scene change and/or exclude at least one specific class of scene change.

12. The method of claim 10, wherein the scene changes are caused by a timewise dynamic development of a contrast agent injection.

13. The method of claim 12, wherein at least two tomographic volumes are prepared, and wherein a first one of the at least two tomographic volumes corresponds to a state of the object without contrast agent and a second one of the at least two tomographic volumes contains only the contrast agent.

14. The method of claim 1, wherein the plurality of x-ray projections and/or projections derived therefrom are displayed within a time sequence.

15. The method of claim 1, wherein a position of a currently displayed x-ray projection and/or derived projection is marked in the representation of the large-area x-ray image.

16. The method of claim 1, wherein a timewise rate for the recording of the plurality of x-ray projections and/or a pulse length of the x-ray device is matched to a velocity and/or an angular velocity of the linear movement.

17. An x-ray device for producing a large-area x-ray image of an object mounted by means of an object platform and producing additional synthetic x-ray projections, comprising:

a C-arm x-ray device; and one or more processors configured by computer-executable instructions to perform the method of claim 1 in conjunction with the C-arm x-ray device.

18. A tangible, non-transitory, computer-readable storage medium having stored thereon a computer program, which can be loaded directly into a memory unit of a control unit of an x-ray device, in particular a C-arm x-ray device, with program segments to execute all steps of the method according to claim 1, when the computer program is executed in the control unit of the x-ray device.

19. A tangible, non-transitory, computer-readable storage medium, having stored thereon program segments that can be read and executed by a computer unit in order to execute all steps of the method according to claim 1, when the program segments are executed by the computer unit.

20. The method of claim 1, further comprising generating, prior to the movement, a preview image comprising the area of interest, wherein the preview image does not correspond to a current relative position of the x-ray device and the object platform.

\* \* \* \* \*